US00PP09930P

United States Patent [19]

Guillou et al.

[11] Patent Number: Plant 9,930

[45] Date of Patent: Jun. 17, 1997

[54] GERANIUM PLANT NAMED 'GUISAINT'

[75] Inventors: Jacques Guillou; Bernard Guillou; Maurice Guillou, all of Saint-Malo, France

[73] Assignee: Ets. Guillou Freres, Saint-Malo, France

[21] Appl. No.: 384,527

[22] Filed: Feb. 1, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Guisaint, characterized by its deep red and double-type flowers; green foliage; slightly visible zonation which forms a ring near the base; and compact and good branching plant habit.

1 Drawing Sheet

The present invention comprises a new and distinct cultivar of geranium, botanically known as *Pelargonium peltatum l'hert* and hereinafter referred to by the cultivar name Guisaint. Guisaint is a product of planned breeding program which had the objective of creating new geranium cultivars with a deep dark-red flower color and compact and well-branched growth habit.

Guisaint was originated from a hybridization made in a controlled breeding program in Saint Malo, Bretagne, France in 1989. The female and male parents were unnamed hybrids from the proprietary Guillou collection, both parents being characterized by dark-red color and semi-double flowers.

Guisaint was discovered and selected as one flowering plant within the progeny of the stated cross by the inventors in 1990 in a controlled environment in Saint Malo, France.

The first act of asexual reproduction of Guisaint was accomplished when vegetative cuttings were taken from the initial selection in 1992 in a controlled environment in Haalderen, The Netherlands, by a technician working under the supervision of the inventors. Horticultural examination of selected units initiaited in September 1992 has demonstrated that the combination of characterisitcs as herein disclosed for Guisaint are firmly fixed and are retained through successive generations of asexual reproduction.

Guisaint has not been observed under all possible environmental conditions. The phenotype may vary with variations in environment such as temperature, light intensity, and daylength with a change in genotype. The following observations, measurments, and comparisons describe plants grown in Haalderen, The Netherlands, under greenhouse conditions which approximate those generally used in commercial practice.

The following traits have been repeatedly observed and are determined to be basic characteristics of Guisaint which in combination distinguish this geranium as a new and distinct cultivar:

1. Red double-type flowers.
2. Medium green foliage.
3. Very weak to weak zonation which forms a ring near the base.
4. Compact plant habit.
5. Good branching habit.

Of the many commercial cultivars known to the present inventors, Guisaint can be closely compared to Phisophie and Fisrom. Guisaint, however, has short internodes while Phisophie has long to very long internodes and Fisrom has medium to long internodes. The markings on the upper petals of Guisaint are relatively conspicuous while they are inconspicuous on Phisophie. The leaf zonation is weak on Guisaint while it is relatively conspicuous on Fisrom.

The accompanying photographic drawings show typical flower and foliage characteristics of Guisaint.

Figure 2:
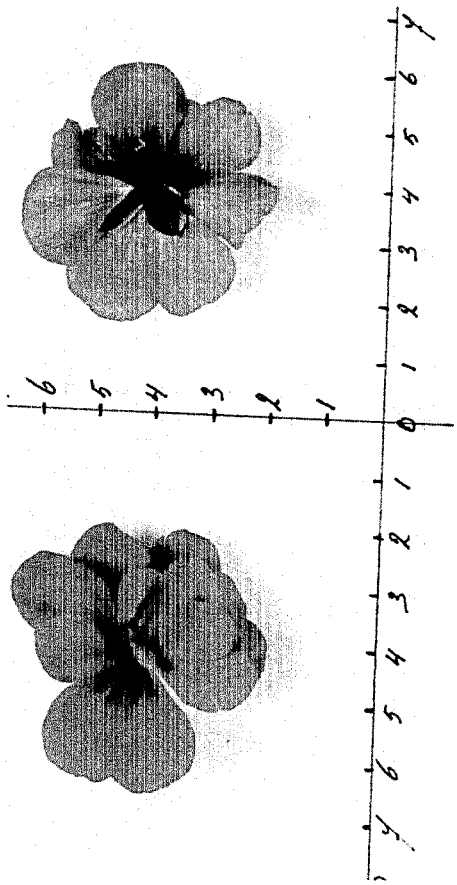
FIG. 2 is a top and bottom view of an individual flower from the cultivar.
Figure 3:
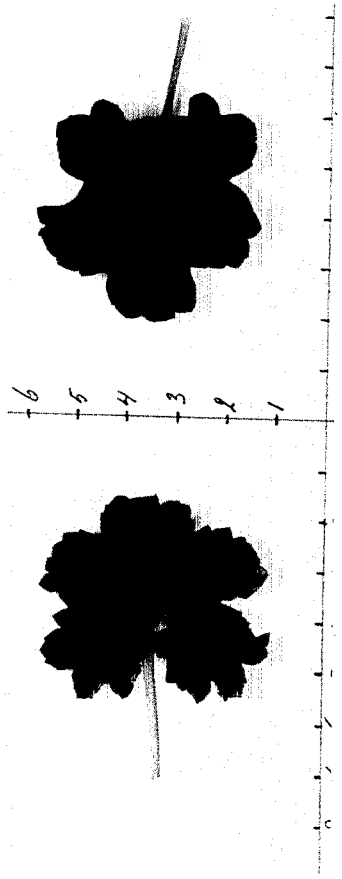
FIG. 3 is a top and bottom view of an individual leaf from Guisaint.
Figure 1:
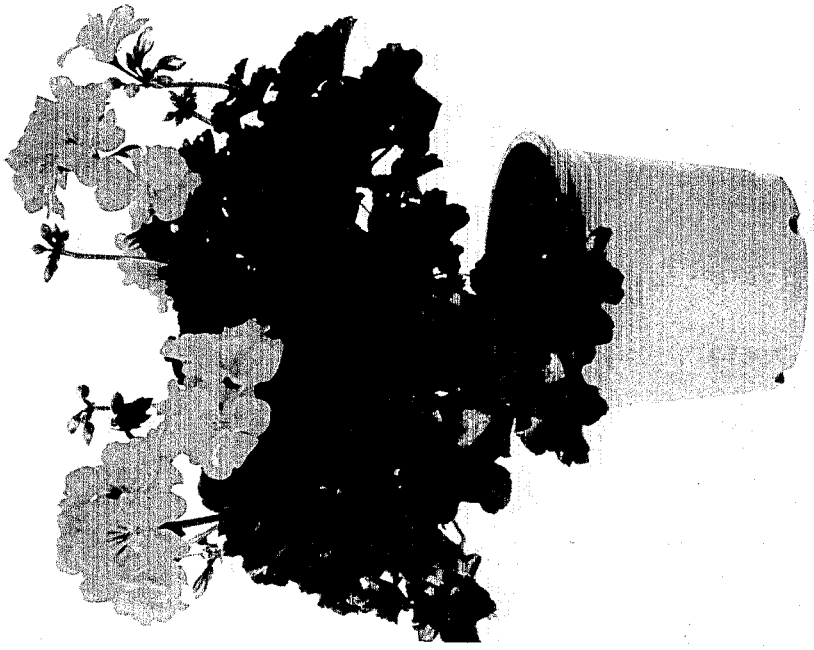
FIG. 1 is a side view of a plant showing open and closed flowers.

In the following description color references are made to The Royal Horticultural Society (R.H.S) Colour Chart. The color values were determined indoors in 1992 under greenhouse conditions at Haalderen, The Netherlands. Colors are as true as possible with illustrations of this type.

Classification:

*Botanical.*—*Pelargonium peltatum l'hert* cv. Guisaint.

*Commercial.*—Ivy geranium Guisaint.

INFLORESCENCE

A. Umbel: Nearly semi-spherical with 4 to 7 buds per umbel.
- *Average diameter.*—100 mm.
- *Average depth.*—38 mm.
- *Peduncle length.*—85 mm.
- *Pedicel length.*—23 mm.

B. Corolla:
- *Average diameter.*—50 mm.
- *Form.*—Double-type with 10 petals.
- *Color (general tonality from a distance of three meters)* .—Deep dark-red.
- *Color (abaxial).*—Dark-red, R.H.S. ca. 46C.
- *Color (adaxial).*—Dark-red, R.H.S. ca. 46C. with very dark-red veins that appear as stripes.
- *Petal size.*—Approximately 15 mm wide and 28 mm long.
- *Petaloid size.*—Approximately 12 mm wide and 20 mm long.
- *Sepal number.*—5.

C. Bud:
- *Shape.*—Elliptic.
- *Color (abaxial).*—Green, no anthocyanin.
- *Color (adaxial).*—Dark-pinkred, R.H.S. ca. 46D.

D. Reproductive organs:
- *Androecium.*—3–7 fertile anthers, white filaments, orange pollen.
- *Gynoecium.*—5–6 lobed stigma, red style stigma.

E. Spring flowering response period: 1.6 flowers per umbel opened 15 weeks after planting of unrooted cuttings (pinched plants).

F. Outdoor flower production: 80 to 90 umbels per plant from late April/May through September/October. Pinching of spent blooms in necessary to ensure continued flowering.

G. Durability: Shatter resistance good.

PLANT

A. Foliage:

*Form.*—Ivy-shaped.

*Margin.*—Entire and serrate.

*Color* (*abaxial*).—Medium-green. I R.H.S. 137A.

*Color* (*abaxial*).—Green.

*Color* (*zonation*).—Reddish-brown that is slightly visible.

*Variegation.*—Absent.

*Margin.—Medium to strong undulation.*

General appearance and form:

*Internode length.*—30 to 40 mm.

*Branching pattern.*—5 to 6 branches per plant that grow upright.

*Height.*—50 to 55 cm. in August.

*Plant vigor.*—The plant is of average vigor and does not grow subsequent to flowering.

C. Tolerance to Botrytis: Good.

What is claimed is:

1. A new and distinct cultivar of geranium plant named Guisaint, as illustrated and described.

* * * * *